United States Patent [19]

Schotland et al.

[11] Patent Number: 5,762,607
[45] Date of Patent: Jun. 9, 1998

[54] EMISSION TOMOGRAPHY SYSTEM AND METHOD USING DIRECT RECONSTRUCTION OF SCATTERED RADIATION

[76] Inventors: John Carl Schotland, 316 Penn Rd., Wynnewood, Pa. 19096; Masaru Ishii, 2429 Locust St. Apt. 610, Phila, Pa. 19103

[21] Appl. No.: 820,613

[22] Filed: Mar. 19, 1997

[51] Int. Cl.$^6$ ..................................................... A61B 5/05
[52] U.S. Cl. .......................... 600/407; 600/476; 356/432
[58] Field of Search ............................. 128/664, 665, 128/633, 653.1; 250/341.1, 358.1; 600/473, 476, 310, 407; 356/432

[56] References Cited

U.S. PATENT DOCUMENTS

| | | |
|---|---|---|
| 3,829,838 | 8/1974 | Lewis et al. .................... 340/172.5 |
| 4,515,165 | 5/1985 | Carroll . |
| 4,948,974 | 8/1990 | Nelson et al. . |
| 5,034,613 | 7/1991 | Denk et al .................... 250/458.1 |
| 5,070,455 | 12/1991 | Singer et al. . |
| 5,090,415 | 2/1992 | Yamashita et al. . |
| 5,148,022 | 9/1992 | Kawaguchi et al. . |
| 5,158,090 | 10/1992 | Waldman et al. . |
| 5,203,339 | 4/1993 | Knuttel et al. . |
| 5,213,105 | 5/1993 | Gratton et al. . |
| 5,275,168 | 1/1994 | Reinties et al. . |
| 5,371,368 | 12/1994 | Alfano et al. .................... 250/341.1 |
| 5,386,827 | 2/1995 | Chance et al. . |
| 5,441,054 | 8/1995 | Tsuchiya ............................. 128/665 |
| 5,451,785 | 9/1995 | Faris .................................. 250/330 |
| 5,528,365 | 6/1996 | Gonatas . |
| 5,640,247 | 6/1997 | Tsuchiya ............................ 356/446 |
| 5,694,938 | 12/1997 | Feng ........................................ 1/1 |

OTHER PUBLICATIONS

"Photon Hitting Density" by Schotland, Haselgrove, Leigh, Feb. 1, 1993.

"Diffusive Emission Tomography" by Schotland and Ishii, Mar. 20, 1996.

*Primary Examiner*—Marvin M. Lateef
*Assistant Examiner*—Eleni Mantis Mercader
*Attorney, Agent, or Firm*—John T. Peoples

[57] ABSTRACT

A method for the direct reconstruction of an object from measurements of the quantum efficiency determined from both a diffusing wave and a reradiated diffusing wave effected by irradiating the object with a source of radiation. The quantum efficiency is related to the number density of the fluorescent source distribution defining the image to be reconstructed by an integral operator. The image of the object is directly reconstructed by executing a prescribed mathematical algorithm, as determined with reference to the integral operator, on the quantum efficiency.

6 Claims, 6 Drawing Sheets

ENABLE SOURCE OF RADIATION AND
MEASURE QUANTUM EFFICIENCY AT DETECTOR ( $\phi(r_1,r_2)$ )

↓ 710

RESTRICT QUANTUM EFFICIENCY DATA
FOR GIVEN SOURCE-DETECTOR GEOMETRY ( Restrict $\phi(r_1,r_2)$ to obtain $\alpha_P(\rho_1,\rho_2)$ )

↓ 720

INTEGRATE RESTRICTED FOURIER TRANSFORM
FOR DETECTOR POSITION TO OBTAIN
REDUCED QUANTUM EFFICIENCY DATA ( $\alpha_P(\rho_1) = \int d^2\rho_2 \alpha_P(\rho_1,\rho_2)$ )

↓ 730

DIRECTLY COMPUTE GENERALIZED INVERSE FROM
SINGULAR VALUES AND EIGENVECTORS
BOTH DETERMINED WITH REFERENCE TO
REDUCED QUANTUM EFFICIENCY DATA ( $K^+(r;\rho_1) = \int d^2q \frac{1}{\sigma_q} g_q^*(\rho_1) f_q(r)$ )

↓ 740

DIRECTLY COMPUTE THE EQUIVALENT NUMBER DENSITY
IMAGE USING GENERALIZED INVERSE AND
REDUCED QUANTUM EFFICIENCY DATA ( $\alpha(r) = \int d^2\rho_1 K^+(r;\rho_1) \alpha_P(\rho_1)$ )

EMISSION TOMOGRAPHY SYSTEM AND METHOD USING DIRECT RECONSTRUCTION OF SCATTERED RADIATION

FIELD OF THE INVENTION

This invention relates generally to a system, and concomitant methodology, for generating an image of an object and, more particularly, to such system and methodology for which the image is directly reconstructed from measurements of reradiation obtained by irradiating the object with a continuous wave source.

BACKGROUND OF THE INVENTION

The inventive subject matter addresses the physical principles and the associated mathematical formulations underlying the direct reconstruction method for optical imaging in the multiple scattering regime. The result is a methodology for the direct solution to the image reconstruction problem. Moreover, the method is generally applicable to imaging with any scalar wave in the diffusive multiple scattering regime and is not limited to optical imaging. However, for the sake of elucidating the significant ramifications of the present invention, it is most instructive to select one area of application of the method so as to insure a measure of definiteness and concreteness to the description. Accordingly, since many biological systems meet the physical requirements for the application of the principles of the present invention, especially emission tomography principles, the fundamental aspects of the present inventive subject matter will be conveyed using medical imaging as an illustrative application of the method.

There have been three major developments in medical imaging over the past 20 years that have aided in the diagnosis and treatment of numerous medical conditions, particularly as applied to the human anatomy; these developments are: (1) the Computer-Assisted Tomography (CAT) scan; (2) the Magnetic Resonance Imaging (MRI); and (3) the Positron Emission Tomography (PET) scan.

With a CAT scanner, X-rays are transmitted through, for example, a human brain, and a computer uses X-rays detected external to the human head to create and display a series of images—basically cross-sections of the human brain. What is being imaged is the X-ray absorption function for unscattered, hard X-rays within the brain. CAT scans can detect, for instance, strokes, tumors, and cancers. With an MRI device, a computer processes data from radio signals impinging on the brain to assemble life-like, three-dimensional images. As with a CAT scan, such malformations as tumors, blood clots, and atrophied regions can be detected. With a PET scanner, the positions of an injected radioactive substance are detected and imaged as the brain uses the substance. What is being imaged is the GAMMA ray source position. Each of these medical imaging techniques has proved invaluable to the detection and diagnosing of many abnormal medical conditions. However, in many respects, none of the techniques is completely satisfactory for the reasons indicated in the following discussion.

In establishing optimal design parameters for a medical imaging technique, the following four specifications are most important. The specifications are briefly presented in overview fashion before a more detailed discussion is provided; moreover, the shortcomings of each of the conventional techniques are also outlined. First, it would be preferable to use a non-ionizing source of radiation. Second, it would be advantageous to achieve spatial resolution on the order of a millimeter to facilitate diagnosis. Third, it would be desirable to obtain metabolic information. And, fourth, it would be beneficial to produce imaging information in essentially real-time (on the order of one millisecond) so that moving picture-like images could be viewed. None of the three conventional imaging techniques is capable of achieving all four specifications at once. For instance, a CAT scanner is capable of high resolution, but it uses ionizing radiation, it is not capable of metabolic imaging, and its spatial resolution is borderline acceptable. Also, while MRI does use non-ionizing radiation and has acceptable resolution, MRI does not provide metabolic information and is not particularly fast. Finally, a PET scanner does provide metabolic information, but PET uses ionizing radiation, is slow, and spatial resolution is also borderline acceptable. Moreover, the PET technique is invasive due to the injected substance.

The four specifications are now considered in more detail. With respect to ionizing radiation, a good deal of controversy as to its effects on the human body presently exists in the medical community. To ensure that the radiation levels are within what are now believed to be acceptable limits, PET scans cannot be performed at close time intervals (oftentimes, it is necessary to wait at least 6 months between scans), and the dosage must be regulated. Moreover, PET is still a research tool because a cyclotron is needed to make the positron-emitting isotopes. Regarding spatial resolution, it is somewhat self-evident that diagnosis will be difficult without the necessary granularity to differentiate different structures as well as undesired conditions such as blood clots or tumors. With regard to metabolic information, it would be desirable, for example, to make a spatial map of oxygen concentration in the human head, or a spatial map of glucose concentration in the brain. The ability to generate such maps can teach medical personnel about disease as well as normal functions. Unfortunately, CAT and MRI report density measurements—electrons in an X-ray scanner or protons in MRI—and there is not a great deal of contrast to ascertain metabolic information, that is, it is virtually impossible to distinguish one chemical (such as glucose) from another. PET scanners have the ability to obtain metabolic information, which suggests the reason for the recent popularity of this technique. Finally, imaging is accomplished only after a substantial processing time, so real-time imaging is virtually impossible with the conventional techniques.

Because of the aforementioned difficulties and limitations, there has been much current interest in the development of a technique for generating images related to properties of living tissue that satisfy the foregoing four desiderata. Accordingly, a technique using low intensity photons would be safe. The technique should be fast in that optical events occur within the range of 10 nanoseconds—with this speed, numerous measurements could be completed and averaged to reduce measurement noise while still achieving the one millisecond speed for real-time imaging. In addition, source and detector equipment for the technique may be arranged to produce necessary measurement data for a reconstruction procedure utilizing appropriately-selected spatial parameters to thereby yield the desired one millimeter spatial resolution. Finally, metabolic imaging with the technique should be realizable if imaging as localized spectroscopy is envisioned in the sense that each point in the image is assigned an absorption spectrum. Such an assignment may be used, for example, to make a map of oxygenation by measuring the absorption spectra for hemoglobin at two different wavelengths, namely, a first wavelength at which hemoglobin is saturated, and a second wavelength at which hemoglobin is de-saturated. The difference of the measurements can yield a hemoglobin saturation map which can, in turn, give rise to tissue oxygenation information.

The first proposals for optical imaging suggested a mathematical approach (e.g., backprojection algorithm) that is similar to that used to generate X-ray computerized tomography images. Light from a pulsed laser is incident on the specimen at a source position and is detected at a detector strategically placed at a point to receive transmitted photons. It is assumed that the earliest arriving photons (the so-called "ballistic photons") travel in a straight line between the source and detector, and the transmitted intensity is used in a mathematical reconstruction algorithm. In effect, only unscattered incident waves are considered as being useful for forming an image of any objects embedded in the specimen and, accordingly, techniques are employed to eliminate scattered light from the detection process, such as arranging a detector with "fast gating time" to only process the earliest arriving photons. However, since it is known that the ballistic photons are attenuated exponentially, if the specimen has a thickness exceeding a predetermined value, imaging is virtually impossible in many practical situations.

The latest proposals for optical imaging are now directed toward imaging systems which use scattered and diffused radiation to reconstruct a representation of the interior of a specimen. Representative of prior art in this field is U.S. Pat. No. 5,070,455 issued to Singer et al (Singer) on Dec. 3, 1991. The system disclosed by Singer uses radiation, such as photons or other particles, which will be scattered to a significant degree by the internal structure of a specimen. In the system, a specimen is irradiated and measurements of the attenuated and scattered radiation are effected at a number of points along the exterior of the specimen. It has been determined by Singer that such measurements are sufficient to determine the scattering and attenuation properties of the various regions inside the specimen. In accordance with the disclosure of Singer, the interior of the specimen is modeled as an array of volume elements ("voxels"). Each voxel in the model of the specimen has scattering and attenuation properties which are represented by numerical parameters that can be mapped so as to generate several images of the interior of the specimen.

The particular technique used by Singer to reconstruct the interior of the specimen can best be characterized as an "iterative" procedure. This procedure is now described in some detail so as to pinpoint its shortcomings and deficiencies. After collecting the imaging data, the scattering and attenuation coefficients for the voxels are assigned initial values, which helps to shorten the computation process—but which is also the characteristic of iterative or non-direct solution to a mathematical minimization problem. Next, the system computes the intensity of light that would emerge from the specimen if the interior of the object were characterized by the currently assigned values for the scattering and attenuation coefficients. Then, the difference between the measured light intensities and the computed light intensities are used to compute an "error function" related to the magnitude of the errors of reconstruction. This error function (also called "cost function" in minimization procedures) is then minimized using a multi-dimensional gradient descent methodology (such as Fletcher-Powell minimization), i.e., the coefficients are modified so as to reduce the value of the error function.

The process of computing exiting light intensities based on the currently assigned values for the scattering and attenuation coefficients, and then comparing the differences between the computed values and measured values to generate a new approximation of the scattering and attenuation properties of the interior of the specimen, continues until the error function falls below a specified threshold. The final values of the scattering and attenuation coefficients from this process are then mapped so as to generate a series of images of the interior of the specimen, thereby depicting the attenuation and scattering characteristics of the specimen's interior—which presumably will disclose both normal and abnormal conditions.

Singer thus discloses a technique to reconstruct an image by inversion using an iterative minimization procedure. Such an approach is more formally characterized as a "heuristic", in contrast to an "algorithm", since no verification or proof of even the existence of a solution using the approach has been offered. There are essentially an infinite number of scattering and attenuation coefficients under such a regime, and there is absolutely no assurance that the particular coefficients determined using the iterative technique are the actual coefficients for the specimen's interior. Moreover, such a heuristic method has a high computational complexity which is exponential in relation to the number of voxels and which is, in turn, a characteristic of difficult optimization problems with many local minima. The computational complexity of such a approach renders the reconstruction method virtually useless for imaging.

There are other approaches presented in the prior art which are closely related to that presented by Singer; these approaches also effect an indirect inversion of the forward scattering problem by an iterative technique which provide little, if any, physical insight.

Representative of another avenue of approach in the prior art is the subject matter of U.S. Pat. No. 5,213,105 issued to Gratton et al (Gratton). With this approach, a continuous wave source of amplitude modulated radiation irradiates an object under study, and radiation transmitted or reflected by the object is detected at a plurality of detection locations, as by a television camera. The phase and the amplitude demodulation of the radiation is detected, and a relative phase image and a demodulation amplitude image of the object are generated from, respectively, the detected relative phase values and detected demodulation amplitudes of the radiation at the plurality of locations. However, while Gratton does generate data from a continuous wave source, there is no teaching or suggestion of a methodology to use the data to directly reconstruct the image from the data—rather the data of Gratton is merely used to obtain and display, separately and independently, the shift in relative phase and the change in modulation of the wavefront of amplitude modulated radiation as a result of propagation of radiation through a scattering medium. Thus, there is no teaching or suggestion in Gratton of how the totality of the spatial modulation and phase data can be combined in a unified approach to directly reconstruct the image. It should be noted that at high modulation frequencies the Gratton procedure is essentially equivalent to ballistic imaging, while at low modulation frequencies an entirely new approach to the reconstruction problem is necessary.

SUMMARY OF THE INVENTION

These limitations and other shortcomings and deficiencies of conventional techniques are obviated, in accordance with the present invention, by utilizing a direct reconstruction emission tomography method, and concomitant system, to generate an image of an object under investigation; the direct reconstruction formulation guarantees both the existence and uniqueness of the imaging technique. Moreover, the direct reconstruction method significantly reduces computational complexity.

In accordance with one broad aspect of the present invention, the object under study is irradiated by a diffusing wave. Then the intensity of a reradiated diffusing wave is measured to determine a quantum efficiency of the diffusing waves, that is, the irradiation diffusing wave and the reradiated diffusing wave, with the quantum efficiency being related to the image by an integral operator. The image is directly reconstructed by executing a prescribed mathematical algorithm, determined with reference to the integral operator, on the quantum efficiency.

In accordance with another broad aspect of the present invention, the object under study is irradiated by a diffusing wave. Then the intensity of a reradiated diffusing wave is measured to determine a quantum efficiency of the diffusing waves, that is, the irradiation diffusing wave and the reradiated diffusing wave, with the quantum efficiency being related to the image by an integral operator. The image is directly reconstructed by executing a prescribed mathematical algorithm, determined with reference to the integral operator, on the quantum efficiency, wherein the algorithm further relates the image to the quantum efficiency by another integral operator.

The organization and operation of this invention will be understood from a consideration of the detailed description of the illustrative embodiment, which follows, when taken in conjunction with the accompanying drawing.

BRIEF DESCRIPTION OF THE DRAWING

The same element appearing in more than one Figure has the same reference numeral.

DETAILED DESCRIPTION

To place in perspective the detailed description of the present invention and thereby highlight the departure from the art as disclosed and claimed herein, it is both instructive and informative to first gain a basic understanding of the imaging environment in which the present invention operates by presenting certain foundational principles pertaining to the subject matter in accordance with the present invention. Accordingly, the first part of the description focuses on a high-level discussion of the imaging systems relevant to the inventive subject matter; this approach has the advantage of introducing notation and terminology which will aid in elucidating the various detailed aspects of the present invention. After this overview, the system aspects of the present invention, as well as the concomitant methodology, are presented with specificity.

Overview of the Present Invention

Multiple scattering of light presents a fundamental physical obstruction to optical imaging. The inventive subject matter of the present invention addresses this phenomena, with the surprising result that reradiated diffusive light from a fluorescent source contains sufficient information to image the fluorescent source distribution of the fluorescent source which has been excited by a diffusive wave. This conclusion obtains from a version of inverse scattering theory that is applicable to multiple scattering in the diffusion limit. Using this representation, the first direct reconstruction procedure ever devised for imaging the fluorescent source distribution embedded in a highly scattering medium probed by diffusing waves is elucidated. In contrast to techniques which utilize unscattered (ballistic) photons for image formation, the procedure in accordance with the present invention allows for the imaging of objects whose size is large compared to the average scattering mean free path.

The familiar opaque or cloudy appearance of many objects having impinging light may be explained by the phenomenon of multiple light scattering. (It is to be noted that terminology will be generalized hereinafter so that an "object" is the physical manifestation of what is under study—such an object may stand alone, may be embedded in a specimen or a sample; in any case, the context of the descriptive material about an object will be set forth with clarity the meaning to be attached to the generic term "object" in that context.) The disclosure and teachings of the present invention address the problem of imaging a fluorescent source object that is embedded in a highly scattering medium, that is, a diffusing wave propagates in a highly scattering medium and excites a distribution of fluorescent molecules in the object to be reconstructed. Since diffusively reradiated light contains sufficient information for direct image reconstruction, the problem can be expressed in a tractable form amenable to an essentially closed-form solution—meaning that there is no need to rely upon or resort to an iterative/minimization-type reconstruction with all its shortcomings and pitfalls.

Figure 1:
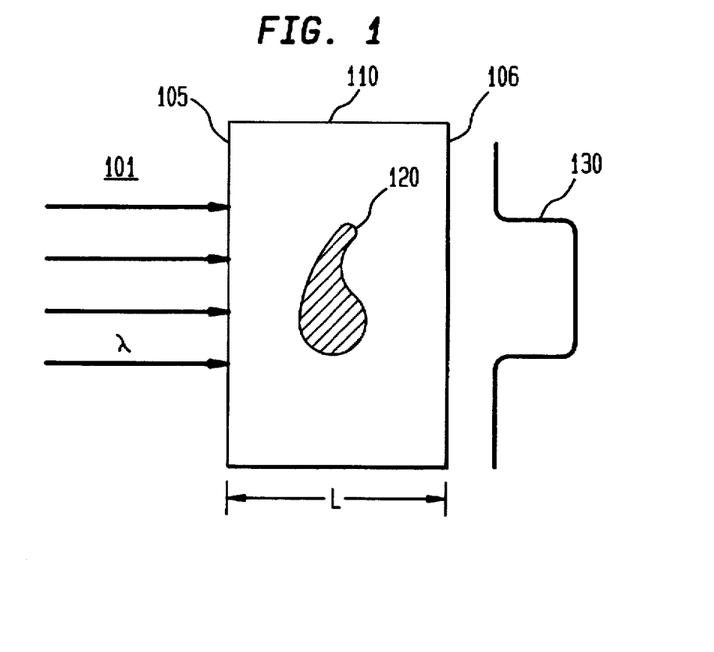
FIG. 1 exemplifies the transmission of light through a specimen containing an absorbing object in the ballistic limit.

For illustrative purposes, the simple, non-fluorescent case of only an absorbing object is considered first so as to elucidate a direct reconstruction process at its most fundamental level. The simplified absorbing system to which direct reconstruction is applicable is one in which a plane wave of light (photons) of wavelength $\lambda$ is incident upon a sample of linear dimension L that contains a spatially-extended object characterized by a position-dependent optical absorption coefficient; the width L is aligned with the impinging incident wave. If it is further assumed that photons are scattered by particles whose size is large compared to $\lambda$, then the scattering is described by a transport mean free path, designated l*; the mean free path characterizes the average distance a photon travels before its direction is randomized. In the single-scattering regime, that is, where l* >>L, it is observed that most of the incident wave is unscattered upon exiting the sample and thus may be used to form a projection image of the absorbing object; this effect is depicted in FIG. 1. In FIG. 1, light rays 101 of wavelength $\lambda$ impinge on front 105 of sample 110 containing absorbing object 120, wherein the light rays transmitted through sample 100 exiting back 106 of sample 110 form a projection image represented by trace 130. The transmitted intensity represented by trace 130 is related to line integrals of the optical absorption coefficient along the direction of propagation of the unscattered wave. This gives rise to the so-called Radon transform of the absorption coefficient. By inversion of the Radon transform, it is possible to recover the absorption function and thus an image of absorber 120 is reconstructed. As already alluded to above, all commercially available imaging techniques are based on this simple physical principle.

Figure 2:
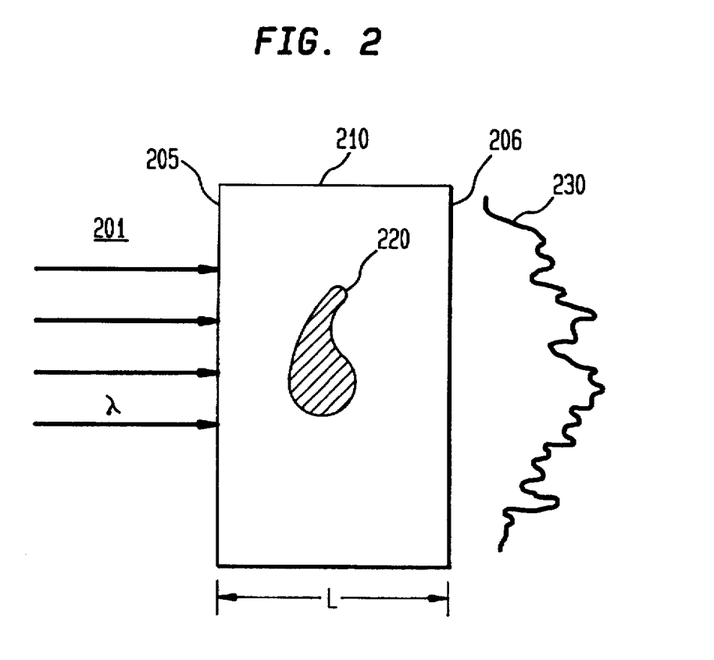
FIG. 2 exemplifies the transmission of light through a specimen containing an absorbing object in the diffusion limit.

In the multiple-scattering regime, that is, where $l^* \ll L$, a wave scatters many times while traversing the sample. In this situation, with $\lambda \ll l^*$, the path of a single photon may be described as a diffusive random walk where $D=\frac{1}{3}(c/n)l^*$ is a suitable diffusion constant, with c being the speed of light, n being the index of refraction, and c/n being the speed of light in the medium of the sample. The unscattered, or ballistic photons, are exponentially attenuated with a static transmission coefficient $T_{ball} \sim \exp(-L/l^*)$. The dominant contribution to the transmitted intensity is provided by diffusive photons with a diffusive transmission coefficient $T_{diff} \sim l^*/L$ which, even with coherent illumination, forms a complicated interference pattern that does not contain a simple image of the sample; such a pattern is illustrated in FIG. 2 (which has essentially the same pictorial representation as FIG. 1, except that the physical system of FIG. 2 is such that $l^* \ll L$ as contrasted to $l^* \gg L$ in FIG. 1). In FIG. 2, light rays 201 of wavelength $\lambda$ impinge on front 205 of sample 210 and eventually exit sample 210 from back 206. Absorbing object 220 gives rise to trace 230, which is representative of the complicated transmitted light pattern exiting back 206. In accordance with the present invention, there is devised a closed-form procedure for utilizing the information in such complicated patterns as exhibited by trace 230 to locate an object and thus perform optical imaging in the multiple-scattering regime.

Indeed, it has frequently been pointed out in the prior art that ballistic photons convey the least distorted image information while diffusive photons lose most of the image information. For this reason several elegant experimental techniques have been designed to select the ballistic photon contribution either by optical gating, holography, or filtering of the diffusive photons by optical absorption. There is, however, an intrinsic physical limitation of any technique that relies solely on ballistic photons. This may be appreciated by considering the exponential attenuation of ballistic photons relative to the mild algebraic attenuation of diffusive photons. In particular, if the sample size L is sufficiently large compared to $l^*$, then $T_{ball}$ will fall below an experimentally measurable threshold (e.g., if $l^*$ is about 0.5 millimeters, then the attenuation is proportional to $e^{-40}$ in only 2 centimeters).

Thus, the likelihood of now reconstructing important and valuable images heretofore believed to be virtually impossible to reconstruct provides a strong motivation to overcome the limitations of ballistic imaging by employing multiply scattered diffusive photons for image reconstruction. From fundamental physical principles, such a reconstruction from the interference pattern of diffusive transmitted light is attainable. In the emission tomography case, such a reconstruction is uniquely determined by one parameter, namely, the fluorescent source distribution as manifested by a "number density" of fluorescent molecules. As presented herein in accordance with the present invention, the "quantum efficiency" (that is, the intensity of the reradiated diffusing wave normalized by the intensity of the diffusing wave that would be measured in the absence of the fluorophore) is related to the number density by an integral equation. Then the number density may be directly reconstructed using a suitable algorithm which references this integral operator. In contrast to ballistic methods, the resulting reconstruction may be used to image samples whose size L is large compared to $l^*$.

Function Theoretic Basis for Emission Tomography

In conventional emission tomography the spatial distribution of a radioactive source is imaged by using a variant of standard tomographic image reconstruction as alluded to in the foregoing description. In the context of the present invention, the terminology "emission tomography" refers to the reconstruction of a fluorescent source distribution which has been excited by a diffusing wave, that is, a diffusing wave propagates in a highly scattering medium and excites a distribution of fluorescent molecules in the object to be reconstructed. The fluorescent molecules, functioning as contrast agents (e.g., indocyanine green), typically have been administered to patients and are taken on by the targeted object. The fluorescent molecules are characterized by a "number density" n(r), which is to be determined from the reconstruction process.

Consider then the propagation of a diffusing wave in a highly scattering medium, characterized by both fluctuations in the absorption and diffusion coefficients. The oscillatory part of the excitation wave energy density, $u_1(r)$, obeys the equation:

$$(\alpha_1 + i\omega + c\sigma n(r) - D_1 \nabla^2)u_1(r) = S(r) \qquad (1)$$

where $\sigma$ is the absorption cross-section of the fluorophore, $\alpha_1$ and $D_1$ are the background absorption and diffusion constants at the excitation wavelength, S(r) is the power density of the excitation source, and $\omega$ is the radian frequency of the source modulation wave—typically, for $\omega=2\pi f$, f is in the radio frequency (RF) range of 100 MHz to 1 GHz.

It is assumed that the modulation frequency is small compared to the decay rate of the excited state of the fluorophore so that the time delay associated with the process of reradiation of a reradiated diffusing wave may be neglected. Then, emission from the object occurs by means of a diffusing wave whose energy density, $u_2(r)$, is governed by:

$$(\alpha_2 + i\omega - D_2 \nabla^2)u_2(r) = u_1(r)\alpha(r), \qquad (2)$$

with $\alpha(r) = \zeta c\sigma n(r)$ being denoted the "equivalent number density", and where $\zeta$ is the quantum yield of the fluorophore, and $\alpha_2$ and $D_2$ denote the background absorption and diffusion constants at the reradiation wavelength. (The more general case where the lifetime (inverse decay rate) $\tau$ of the excited state is no longer restricted to obey the condition $\omega\tau \ll 1$ is readily treated by modifying $\alpha(r)$ so that now $\alpha(r) = \zeta c\sigma n(r)/(1+i\omega\tau(r))$. Note that now both n(r) and $\tau(r)$ may be recovered once $\alpha(r)$ has been reconstructed.)

In general, the so-called quantum efficiency, $\phi(r_1, r_2)$, of a diffusing wave generated by a point source at $r_1$ and detected at $r_2$ is defined as the intensity of the reradiated diffusing wave normalized by the intensity of the diffusing wave that would be measured in the absence of the fluorophore. An integral equation for the quantum efficiency may be derived from the perturbative solution to equation (2), which to lowest order is of the form:

$$\phi(r_1, r_2) = \int d^3 r \Gamma(r; r_1, r_2)\alpha(r) \qquad (3)$$

where $$\Gamma(r;r_1,r_2) = \frac{1}{G_1^{(0)}(r_1,r_2)} G_1(r_1,r) G_2^{(0)}(r,r_2) \quad (4)$$

is the "number density kernel". Here, $G_1(r_1,r_2)$ and $G_2^{(0)}(r_1,r_2)$ refer to the diffusion Green's functions for equations (1) and (2), and $G_1^{(0)}(r_1,r_2)$ denotes $G_1(r_1,r_2)$ evaluated in the absence of the fluorophore. The Green's function of an infinite medium is given by:

$$G_l^{(0)}(r,r') = \frac{\exp[-k_l|r-r'|]}{4\pi D_l|r-r'|},$$

where $$k_l = \left(\frac{\alpha_l + i\omega}{D_l}\right)^{\frac{1}{2}}$$

with l=1,2 being the wave numbers of the excitation and emission diffusing waves.

Equation (3) is an exact expression for the quantum efficiency that may be used to generate a perturbative expansion in $\alpha(r)$. To the lowest order in $\alpha(r)$, equation (4) becomes:

$$\Gamma(r;r_1,r_2) = \frac{1}{G_1^{(0)}(r_1,r_2)} G_1^{(0)}(r_1,r) G_2^{(0)}(r,r_2). \quad (5)$$

In the image reconstruction problem in accordance with the present invention, the source number density n(r), via $\alpha(r)$, is recovered from the intensity of the excitation and emission diffusing waves measured on the surface surrounding the object as manifested by the quantum efficiency. The next three sub-sections each provide a direct reconstruction solution technique for integral equation (3). The first approach to solving the reconstruction problem involves a direct numerical solution to integral equation (3). The next approach involves the construction of an explicit inversion formula for integral equation (3) using analytic singular value decomposition. The last approach also involves the construction of an explicit inversion formula for integral equation (3) using a Fourier Transform technique.

In each of the three cases, the analysis assumes that the object is immersed in an effectively infinite homogeneous medium whose diffusion and absorption coefficients are taken to be identical to the object. The most general case wherein the diffusion and absorption coefficients are different from the object will be readily contemplated by one with ordinary skill in the art based on the teachings of the homogeneous case.

(A) DIRECT NUMERICAL SOLUTION OF INTEGRAL EQUATION (3)

A.1 METHODOLOGY

A.1.1 Computational Model

The fundamental integral equation expressed by equation (3), repeated here, $$\phi(r_1,r_2) = \int d^3r \Gamma(r; r_1; r_2)\alpha(r), \quad (3)$$

is in the form of a Fredholm equation of the first kind. Such equations are typically written in the form $Kf=g$, or $$\int K(x,x')f(x')d^3x' = g(x) \quad (6)$$

where f,g are elements of appropriately selected function spaces. Equation (6) is said to be ill-posed if (a) it is not solvable, (b) a unique solution does not exist, or (c) the solution does not depend continuously on the data. The latter case (c) is of primary interest in the numerical study of ill-posed problems because it may lead to numerical instability. This is particularly important if the data is imprecisely known or is the subject to statistical uncertainties, such as measurement inaccuracy or noise, which would be the situation for measurements for imaging. There are methods for conditioning ill-posed problems. First, if the solution does not exist, the minimizer of $\|Kf-g\|$ is defined as a solution. Non-uniqueness is handled by choosing the minimizer with the least norm. Finally, continuity is restored by introducing "regularization" to the solution procedure.

Solving for the minimizer with the least norm yields the "normal equation" relating to equation (6); the normal equation is of the form $$K^*Kf = K^*g, \quad (7)$$

where $K^*$ is the adjoint of K, and the property that $K^*K$ is self-adjoint has been employed. Thus, a solution for f in equation (6) is of the following form:

$$f = (K^*K)^{-1}K^*g \equiv^+ g. \quad (8)$$

From equation (8), $$K^+ = (K^*K)^{-1}K^* \quad (9)$$

is called the "generalized inverse" of K.

A.1.2 Singular Value Decomposition

If K is such that a mapping from $H_1$ to $H_2$ occurs, where $H_1$ and $H_2$ are Hilbert spaces, then $K^*K$ is a self-adjoint, positive operator. If the eigenfunctions and eigenvalues of $K^*K$ are denoted by $\{f_n\}$ and $\{\sigma_n^2\}$, respectively, then the following relation obtains: $K^*Kf_n = \sigma_n^2 f_n$.

The $\{\sigma_n\}$ are the singular values of K. Also, the $\{f_n\}$ form a basis for $H_1$. The singular values are ordered as $\sigma_1^2 \geq \sigma_2^2 \geq \ldots \geq 0$, where multiplicities are counted and 0 can appear with infinite multiplicity.

If $\{g_n\}$ is defined by $$Kf_n = \sigma_n g_n \quad (10)$$

then the $\{g_n\}$ are a basis for Hilbert space $H_2$. Moreover, it then follows that $$K^*g_n = \sigma_n f_n. \quad (11)$$

To derive the singular value decomposition of K, put K in the form $$K = I_{H2} K I_{H1} \quad (12)$$

and use the identities $$I_{H1} = \sum_n f_n \otimes f_n \quad (13)$$

and $$I_{H2} = \sum_n g_n \otimes g_n, \quad (14)$$

where $\otimes$ denotes the tensor product. Manipulation of equations (12)–(14) leads to $$K = \sum_n \sigma_n g_n \otimes f_n. \quad (15)$$

Equation (15) is called the "singular value decomposition" of K.

The singular value decomposition of equation (15) can now be used to obtain a form for the generalized inverse $K^+$ of equation (9). As a result of equation (15), $$K^*K = \sum_n \sigma_n^2 f_n \otimes f_n \qquad (16)$$

and $$K^* = \sum_n \sigma_n f_n \otimes g_n, \qquad (17)$$

then it directly follows, after substitution of equations (16) and (17) into equation (9), that $$K^+ = \sum_n \frac{1}{\sigma_n} f_n \otimes g_n. \qquad (18)$$

Now, using equations (8) and (18), the solution of Kf=g is f=$K^+$g, which is of the form $$f = \sum_n \frac{1}{\sigma_n} <g_n, g> f_n. \qquad (19)$$

If some of the $\sigma_n$'s vanish, then $K^+$ is not well-defined and, in particular, is not continuous. To resolve this anomaly, the regularization procedure is introduced.

A.1.3 Regularization

To condition the singular value decomposition, the following expression is now defined:

$$K_\beta^+ = \sum_n R_\beta(\sigma_n) f_n \otimes g_n, \qquad (20)$$

where the regularizer R[<i]nf62(σ) has the properties (i) $R_\beta(\sigma) = 1/\sigma$ as $\beta \to 0^+$;

(ii) $R_\beta(\sigma) \sim 1/\sigma$ for $\sigma \gg 0$ (with $\beta > 0$); (21)

(iii) $R_\beta(\sigma) \to 0$ as $\sigma \to 0$ (with $\beta > 0$)

For instance, two natural choices (others are possible) include:

(a) $R_\beta(\sigma) = 1/\sigma$ for $\sigma > \beta$; otherwise, $R_\beta(\sigma) = 0$; (22)

(b) $R_\beta(\sigma) = \sigma/(\beta + \sigma^2)$. (23)

(One typical heuristic criterion is to set $\beta \sim O(\sigma_1)$).

Thus the solution of equation (6) may be written as $$f(x) = \int d^3 x' K_\beta^+(x, x') g(x') \qquad (24)$$

where $$K_\beta^+(x, x') = \sum_n R_\beta(\sigma_n) f_n(x) g_n(x'). \qquad (25)$$

A.1.4 Direct Numerical Solution

The above developments for the formal solution of a general Fredholm equation of the first kind, including the techniques of singular value decomposition and regularization, may now be applied to implement the direct numerical solution of equation (3)

$$\phi(r_1, r_2) = \int d^3r \, \Gamma(r; r_1, r_2) \alpha(r) \qquad (3)$$

with the formal solution as follows:

$$\alpha(r) = \int d^3r_1 d^3r_2 \Gamma_\beta^+(r; r_1, r_2) \phi(r_1, r_2) \qquad (26)$$

where $$\Gamma_\beta^+(r; r_1, r_2) = \sum_n R_\beta(\sigma_n) f_n(r) g_n(r_1, r_2). \qquad (27)$$

For a three-dimensional object, denoted $\Omega$, it is supposed that there are P sources and Q detectors used to probe the object. These sources are spaced about the periphery of the object and, operating in conjunction with the sources, there are suitably placed detectors. For the sake of simplicity, a single frequency is considered in the following exposition. In general, the results may be readily extended to the case of multiple frequencies. Let i, i=1,2, . . . ,P and j, j=1,2, . . . , Q be indices corresponding to the P sources and Q detectors; then, for a given frequency, equation (3) becomes:

$$\phi_{ij} = \int_\Omega d^3r \, \Gamma_{ij}(r) \alpha(r), \qquad (28)$$

where $\phi_{ij}$ and $\Gamma_{ij}(r)$ denote $\phi(r_1, r_2)$ and $\Gamma F(r; r_1, r_2)$ evaluated at the $i^{th}$ source and $j^{th}$ detector positions. Now $\Gamma$ and $\alpha$ are discretized by decomposing $\Omega$ into "voxels" (i.e., volume elements having basically equal sides) $B_m$, m=1,2, . . . , M which cover the object. It is then assumed that the granularity is such that $\alpha$ and $\Gamma$ are constant in each box. To recast equation (28) in a standard form, the following identifications are made:

$$|B_m| \Gamma_{ij}(r_m) \equiv A_{ij}^m, \qquad (29)$$

and $$\alpha(x_m) \equiv a_m, \qquad (30)$$

where $|B_m|$ is the volume of a voxel, and $a_m$ is the strength of $\alpha(x_m)$ at the middle of the $m^{th}$ voxel. Then, using these definitions, equation (28) becomes $$\sum_m A_{ij}^m a_m = \phi_{ij}. \qquad (31)$$

for m=1,2, . . . ,M; i=1,2, . . . ,P; and j=1,2, . . . ,Q. In matrix form, equation (31) is represented as Aa=b, where A is a (PQ by M) matrix, so equation (31) gives PQ equations in M unknowns. Thus, there must be at least as many source-detector pairs (PQ) as voxels (M). It is preferable to "over-determine" equation (31) by having PQ>M, or by using multiple frequencies for each source-detector pair. If there are K frequencies, then matrix A is a (KPQ by M) matrix. Typically in practice KPQ=3M. There are many possible ways to arrange for desired number of frequency measurements. For instance, it is possible to fix $\omega$, and arrange for multiple sources and detectors each operating at $\omega$, but only operate one source at a time. As another example, it is possible to vary $\omega$, and arrange for multiple sources and detectors, each detector being arranged to detect the changes in $\omega$ (e.g., by selecting one of a plurality of band-pass filters), but only operate one source at a time. Finally, it is possible to employ multiple frequencies emitted by multiple sources, and a single detector tuned simultaneously to each of the multiple frequencies, with all sources operating simultaneously.

The solution of singular value decomposition applied to a matrix formulation is a well-known technique. For example, a procedure for singular value decomposition is described in the text "Numerical Recipes", by Press, Flannery, Teukolsky, and Vettering, 1986, Cambridge University Press, Cambridge, England. A commercially available software package implementing the singular value decomposition, called Interactive Data Language (IDL) available from Research Systems Inc. of Denver, Colo., may be used in practice; IDL was specifically designed for scientific computations, especially image processing applications. With IDL, a subroutine-like call of the form "SVD [Matrix]" I (e.g. SVD [A] in terms of the above A matrix) returns the singular values as well as the quantities, denoted the projection operators, from which $\{f_n\}$ and $\{g_n\}$ obtain.

Once the singular value decomposition has been effected, regularization according to equation (25) is readily accomplished in order to obtain the regularized, generalized inverse which, for the matrix A, is denoted $A^+$. The solution to the discretized integral equation (3) becomes $a=A^+b$.

Figure 6:
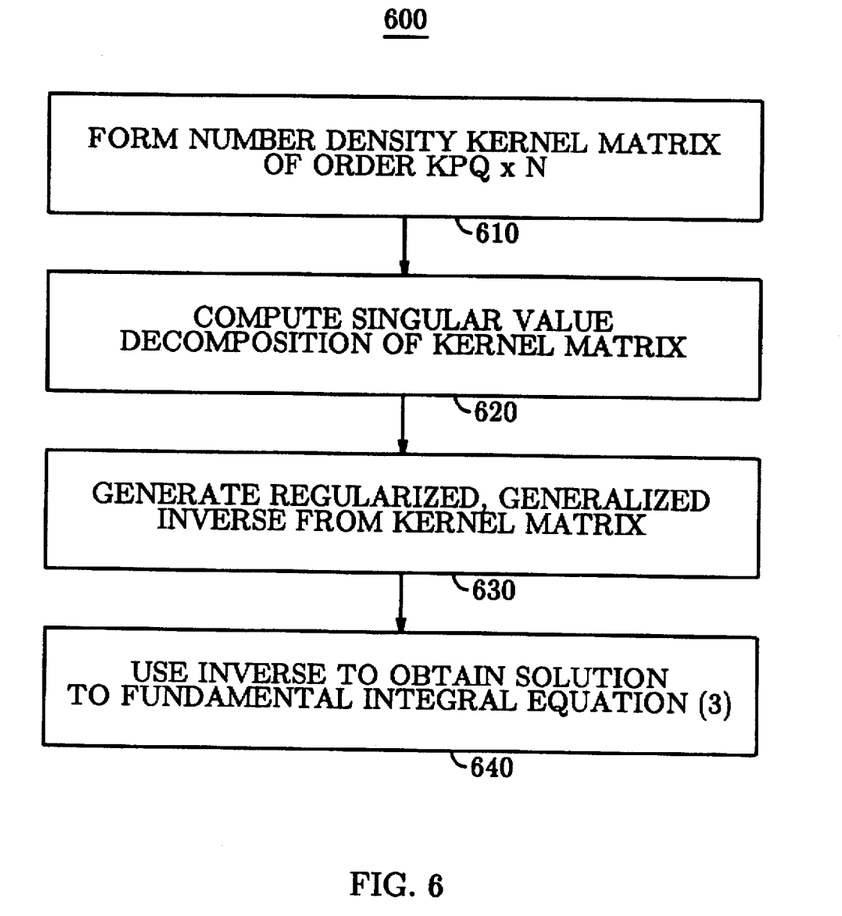
FIG. 6 is a flow diagram for carrying out the direct reconstruction as exhibited by FIG. 5.

The system and methodology described utilizes the free-space model of the absorption kernel (equation (9)) so that the kernel is pre-computed and stored in computer processor 650 for recall during the reconstruction process.

This is appropriate when object 610 is surrounded by an arrangement, such as a thin, rubber-like container filled with a substance (e.g., the commercially available medical product called Intralipid), so that the arrangement provides a spatial extent external to the object that effectively gives rise to a free-space condition surrounding the object. The object's actual boundary (e.g., a human skull during imaging of brain) becomes merely another shape that is determined by the direct reconstruction procedure. Intralipid is useful because it is a colloidal substance wherein particles in the range of 0.5 microns to 2 microns are suspended, and the substance, as packaged, does not rapidly deteriorate; moreover, the l* of such a substance is readily measurable.

(B) ANALYTICAL INVERSION—Analytic Singular Value Decomposition

Figure 3:
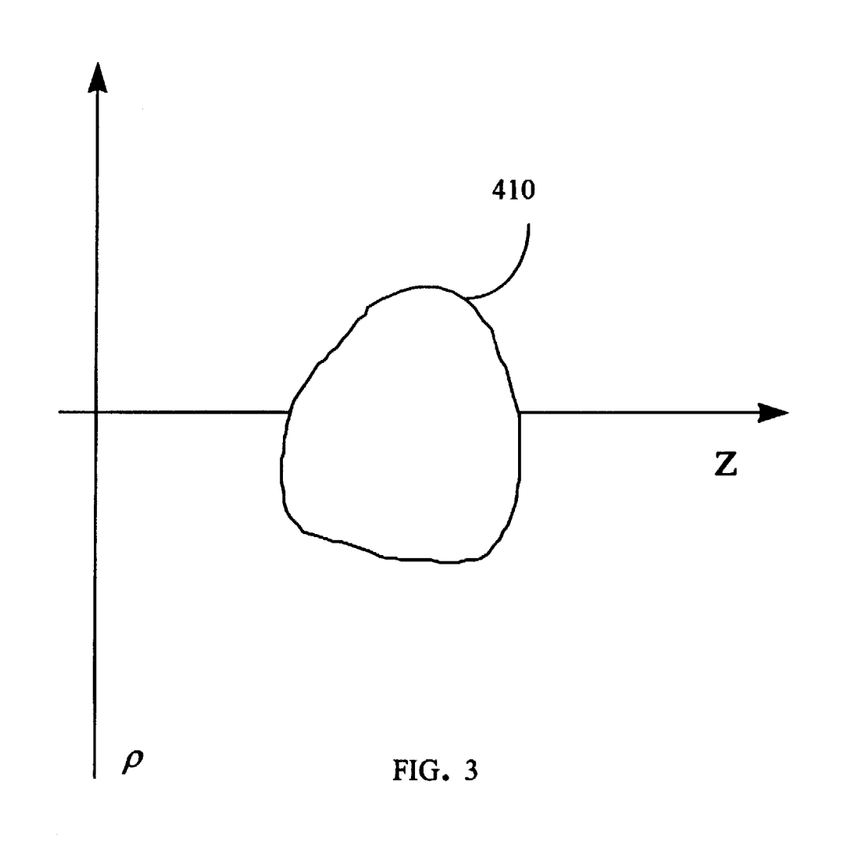
FIG. 3 depicts a sample occupying the half-space z>0, with source(s) and detector(s) located on the plane z=0.

For this sub-section, the following geometry is considered: the object occupies the half-space $z>0$ with sources and detectors being located on the plane $z=0$, as depicted in FIG. 3. Other geometries may also be readily treated by the teachings of this illustrative geometry.

To facilitate the discussion, equation (3), using equation (5), is rewritten in the form:

$$\bar{\alpha}(r_1,r_2) = \int d^3 r G_1^{(0)}(r_1,r) G_2^{(0)}(r,r_2) \alpha(r) \quad (3a)$$

where $\bar{\alpha}(r_1,r_2) = G_1^{(0)}(r_1,r_2)\phi(r_1,r_2)$ is the equivalent quantum efficiency data. The Green's function of an infinite medium is as given previously.

The transverse coordinates of the source and detector are denoted by $\rho_1$ and $\rho_2$, whereas the restrictions of $\bar{\alpha}(r_1,r_2)$ and $G_1^{(0)}(r_1,r)G_2^{(0)}(r,r_2)$ to these coordinates are denoted by $\alpha_p(\rho_1,\rho_2)$ and $K(r;\rho_1,\rho_2)$, respectively. The image reconstruction technique is composed of solving integral equation (3a) in the following form:

$$\alpha_p(\rho_1,\rho_2) = \int d^3 K(r;\rho_1,\rho_2)\alpha(r) \quad (3b)$$

when $\alpha_p(\rho_1,\rho_2)$ is specified, that is, measured. It is observed by integrating over detector positions in integral equation (3b) leads to an integral equation for the "reduced quantum efficiency data", $\alpha_p(\rho_1)$, of the form:

$$\alpha_p(\rho_1) = \int d^3 r K(r;\rho_1)\alpha(r) \quad (32)$$

where $\alpha_p(\rho_1) = \int d^2\rho_2 \alpha_p(\rho_1,\rho_2)$. The kernel $K(r;\rho_1)$ admits the singular value decomposition as outlined in the previous sub-section (A), with $$K(r;\rho_1) = \int d^2 q \, \sigma_q g_q(\rho_1) f_q^*(r), \quad (33)$$

where $$g_q(\rho) = \frac{1}{2\pi} e^{iq\cdot\rho}, \quad (34)$$

$$f_q(r) = \frac{1}{2\pi} ((q^2+k_1^2)^{\frac{1}{2}} + k_2)^{\frac{1}{2}} e^{iq\cdot\rho} \exp[-((q^2+k_1^2)^{\frac{1}{2}} + k_2)|z|], \quad (35)$$

and the singular values $\sigma_q$ are given by $$\sigma_q = \frac{1}{4D_1 D_2 k_2} (q^2+k_1^2)^{-\frac{1}{2}} ((q^2+k_1^2)^{\frac{1}{2}} + k_2)^{-\frac{1}{2}}, \quad (36)$$

where $k_l = ((\alpha_l + i\omega)/D_l)^{1/2}$ with $l=1,2$ being the wave numbers of the excitation and emission/reradiated diffusing waves.

Equation (33) defines the singular value decomposition of $K(\rho_1,r)$ with singular values $\sigma_q$ since $K^*Kf_q=(\sigma_q)^2 f_q$ and $Kf_q=\sigma_q g_q$. This result may then be used to obtain the solution to integral equation (32) in the form:

$$\alpha(r) = \int d^2\rho_1 K^+(r;\rho_1)\alpha_p(\rho_1) \quad (37)$$

where $$K^+(r;\rho_1) = \int d^2 q \frac{1}{\sigma_q} g_q^*(\rho_1) f_q(r). \quad (38)$$

Here, $K^+(r;\rho_1)$ denotes the generalized inverse of $K(r;\rho_1)$. Combining equations (37) and (38), an inversion formula for $\alpha(r)$, which is proportional to the number density $n(r)$, is obtained as follows:

$$\alpha(r) = \quad (39)$$

$$\int d^2\rho_1 \int \frac{d^2 q}{(2\pi)^2} e^{iq\cdot(\rho-\rho_1)} 4D_1 D_2 k_2 ((q^2+k_1^2)^{\frac{1}{2}} ((q^2+k_1^2)^{\frac{1}{2}} + k_2) \times$$

$$\exp[-((q^2+k_1^2)^{\frac{1}{2}} + k_2)|z|] \alpha_p(\rho_1).$$

Several comments on the inversion formula are enlightening. First, observe for large $|q|$ that the singular values of M are asymptotically given by $\sigma_q \sim |q|^{-3/2}$. Thus, the inverse is ill posed, but only mildly so. This, however, is of no concern since cutting off the wavevector integration for large magnitudes of q regularizes the inverse problem. Note that regularization here has a natural physical interpretation. Cutting off the q-integration for $|q|>2\pi/l^*$ simply sets the spatial resolution of the reconstruction to be l*—the length scale on which the diffusion approximation is valid.

Second, the inversion formula may be used to develop a practical image reconstruction algorithm. The simplest approach was already deployed in sub-section (A) wherein a direct numerical implementation was utilized. It is important to appreciate that this algorithm has a computational complexity $O(N^2)$, where N is the number of pixels in the image.

Finally, the proposed algorithm should be compared with the $O(N^3)$ complexity of direct numerical inversion of integral equation (3) by singular value decomposition.

(C) ANALYTICAL INVERSION—Fourier Transform

Equation (3a) is again considered as the starting point of the following discussion:

$$\bar{\alpha}(r_1,r_2) = \int d^3 r G_1^{(0)}(r_1,r) G_2^{(0)}(r,r_2) \alpha(r) \quad (3a)$$

For the discussion of this sub-section, the following geometry is considered: the object occupies the half-space $z>0$ with sources and detectors being located on the plane $z=0$, as depicted in FIG. 3. To this end, let $\rho_1$, $\rho_2$ be the transverse coordinates of the source and detector and let $\alpha_p$ ($\rho_1,\rho_2$) be the restriction of $\overline{\alpha}(r_1,r_2)$ to the measurement surface. The image reconstruction problem thus comprises solving integral equation (3a) when $\alpha_p$ ($\rho_1,\rho_2$) is specified.

Proceeding, consider the Fourier Transform of $\alpha_p$ ($\rho_1,\rho_2$) which is defined by:

$$\hat{\alpha}_p(q_1,q_2) = \int d^2\rho_1 d^2\rho_2 \exp[i(q_1 \cdot \rho_1 + q_2 \cdot \rho_2)]\alpha_p (\rho_1,\rho_2). \quad (40)$$

Equation (3a) thus becomes:

$$\hat{\alpha}_p(q_1,q_2) = \quad (41)$$

$$\frac{1}{4D_1D_2} \int d^3r e^{i(q_1+q_2)\cdot r} ((q_1^2+k_1^2)^{-\frac{1}{2}} ((q_2^2+k_2^2)^{-\frac{1}{2}}) \times$$

$$\exp[-((q_1^2+k_1^2)^{\frac{1}{2}} + (q_2^2+k_2^2)^{\frac{1}{2}})z]\alpha(r),$$

where the following identity has been used:

$$G_1^{(0)}(\rho,0;r') = \quad (42)$$

$$\frac{1}{2D_1}\int \frac{d^2q}{4\pi^2} e^{iq\cdot(\rho-\rho')} (q^2+k_1^2)^{-\frac{1}{2}} \exp[-(q^2+k_1^2)^{\frac{1}{2}} z'],$$

which follows from the Fourier Integral representation of $G_1^{(0)}(r,r')$.

It is advantageous to introduce an invertible transformation from the four-dimensional wavevector space into a four-dimensional parameter space defined by:

$$q = q_1 + q_2$$
$$u_1 = 2(q_1^2+k_1^2)^{1/2}$$
$$u_2 = 2(q_2^2+k_2^2)^{1/2}$$

after equation (41) becomes $$D_1D_2u_1u_2A(q,u_1,u_2) = \int d^3r e^{iq\cdot r}\exp\left[\frac{-(u_1+u_2)z}{2}\right]\alpha(r), \quad (43)$$

where $A(q,u_1,u_2)$ refers to $\hat{\alpha}_p$ ($q_1,q_2$) evaluated in the new coordinates. If attention is now restricted to the three-dimensional surface defined by $u_1=u_2=u$, then equation (43) becomes:

$$D_1D_2u^2A(q,u,u) = \int d^3r e^{iq\cdot r} e^{-uz}\alpha(r) \quad (44)$$

Finally, inverting the Fourier Transform in equation (44) yields the following:

$$\alpha(r) = \int \frac{du}{2\pi i} e^{uz} \int \frac{d^2q}{4\pi^2} e^{-iq\cdot \rho} D_1D_2u^2A(q,u,u), \quad (45)$$

which gives the unique solution to the image reconstruction problem. Note that in the inversion equation (44) that $A(q,u,u)$ must be analytically continued into the complex u-plane since the scattering data only determines $A(q,u,u)$ for u along the positive real axis. Alternatively, the Fourier-Laplace transform may be directly inverted for real u without recourse to numerical analytic continuation.

The spatial resolution is in practice controlled by the available number and relative spacings of sources and detectors. In principle, however, the resolution is limited only by the length scale on which the diffusion approximation is valid. This result is somewhat unexpected since it is anticipated from geometrical optics that the special resolution of the reconstructed image should be c optics that the spatial resolution of the reconstructed image should be controlled by the wavelength of the diffusing wave (which is typically of order the object size). This apparent inconsistency may be resolved by observing that the diffusion tomography experiment is carried out in the near field of the diffusing wave even though it is the far field of the electromagnetic wave which is measured at the detector(s).

Two comments about this image reconstruction algorithm are necessary. First, it is important to appreciate that the algorithm has computational complexity $O(N^2)$ where N is the number of pixels in the image. This includes both the cost of computing the Fourier Transform by fast summation and the cost of obtaining the data in the transformed coordinates. The $O(N^2)$ complexity should be compared to the $O(N^3)$ complexity of direct numerical inversion by singular value decomposition as formulated in sub-section (A). Second, the inverse problem may be expected to be ill-conditioned since inversion of the Fourier Transform is known to be numerically unstable. However, experiments have shown that this is not a serious problem.

D. SYSTEM

Figure 4:
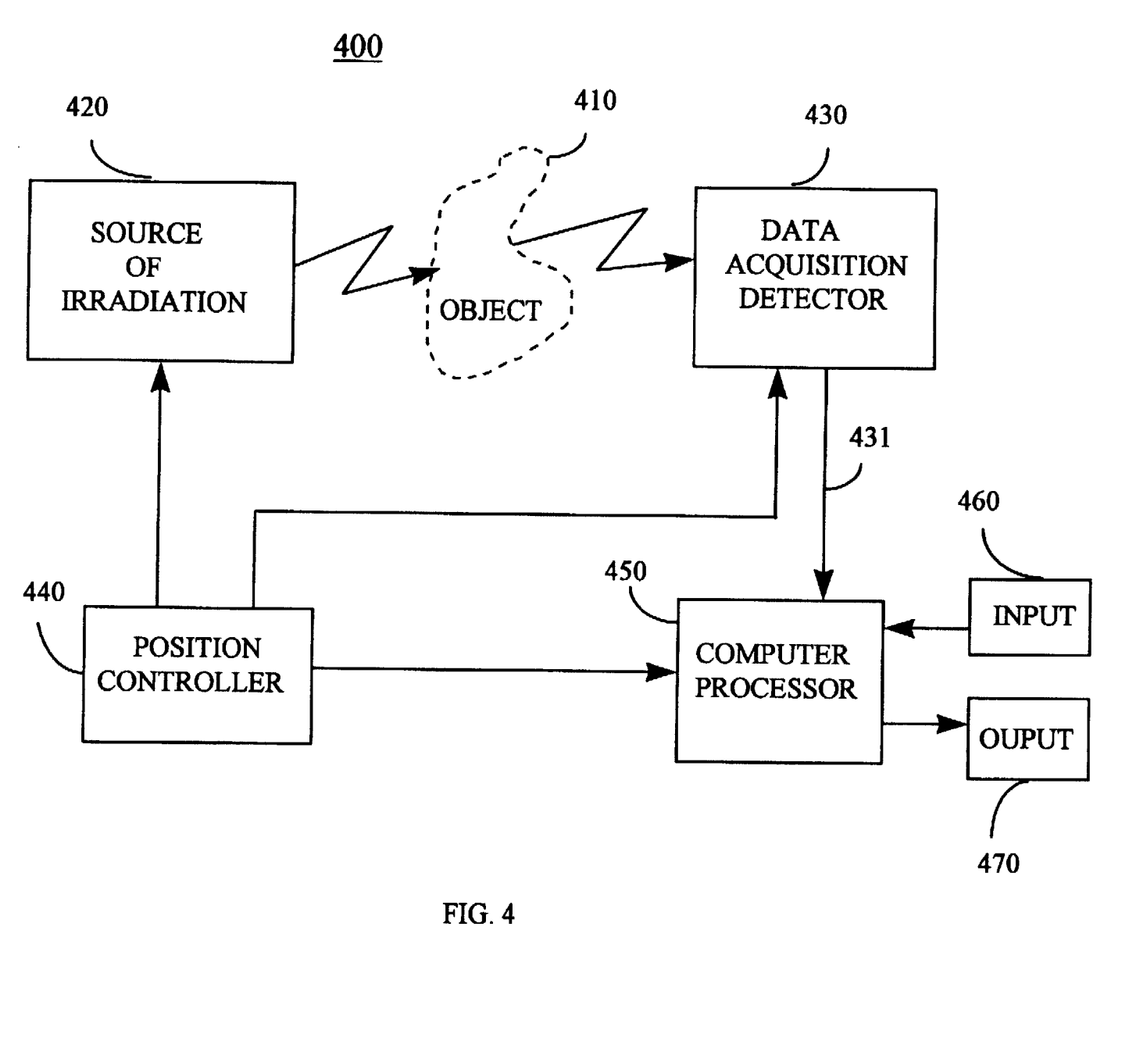
FIG. 4 illustrates a high-level block diagram of an illustrative embodiment of the emission tomography system in accordance with the present invention.

As depicted in high-level block diagram form in FIG. 4, system 400 is a direct reconstruction imaging system for generating an image of an object using measurements of transmitted radiation (e.g., photons) emitted from an object in response to photons impinging on the object. In particular, object 410 is shown as being under investigation. System 400 is composed of: CW source 420 for irradiating object 410; data acquisition detector 430 for generating the quantum efficiency of radiation emitted by object 410 at one or more strategic locations proximate to object 410, such quantum efficiency being determined from measurements of both the original diffusing wave and the reradiated diffusing wave position controller 440 for controlling the location of detector 430 relative to source 420; and computer processor 450, having associated input device 460 (e.g. a keyboard) and output device 470 (e.g., a graphical display terminal). Computer processor 450 has as its inputs positional information from controller 440 and the measured quantum efficiency from detector 430.

Source 420 and data acquisition detector 430 of system 400 are realized with conventional components. For example, CW source 420 is composed of a conventional near infrared laser operating in the 600 to 1200 nm region and at a power level of approximately 10 watts such as provided by a mode-locked Neodymium YAG laser (Antares, model 76S-ML-SHG). Detector 430 is, for instance, composed of a image intensifier (such as provided by Princeton Instruments, Inc., OMA detector model IRY512 G/RB) which feeds a CCD-type television camera (such as provided by ITT, Fort Wayne, Ind., model CCD F144). Moreover, detector 430 is arranged with a conventional adjustable narrow-band interference type filter so as to detect intensities at the wavelengths of both the original diffusing wave (equation (1)) and the reradiated diffusing wave (equation (2)).

Position controller 440 is utilized whenever CW source 420 and/or data acquisition detector 430 may be composed of a plurality of radiation sources and detectors, respectively, in order to control which of the plurality of sources may be energized for a given time period and which of the plurality of detectors may be activated during a prescribed time interval. As will be discussed in more detail below, in a practical implementation of the direct reconstruction imaging technique, it is oftentimes necessary to measure the transmitted intensity effected by a number of source-detector positions surrounding object 410. For the sake of expediency, generation of the required transmitted intensity data is expeditiously accomplished by having arrays of P laser sources and Q photon detectors. Accordingly, source 420 may be composed, in its most general implementation, of P CW sources or the like arranged strategically around the periphery of object 410. Similarly, data acquisition detector may be composed, in its most general realization, of Q radiation detectors or the like also arranged strategically around the periphery of object 410 and in a cooperative relation with the P sources.

The point of departure between the inventive subject matter herein and the prior art resides in the processing of the measured data. Computer 450 stores a computer program which implements the direct reconstruction algorithm. In particular, as illustrated in the foregoing sub-section (A), the stored program processes the measured quantum efficiency data to produce the image of the object under study using a prescribed mathematical algorithm—the algorithm is determined with reference to the integral operator relating the quantum efficiency data to equivalent number density (equation (3)). Also, as illustrated in the foregoing sub-sections (B) and (C), the stored program processes the measured quantum efficiency data to produce the image of the object under study using a prescribed mathematical algorithm—the algorithm is determined with reference to the integral operator relating the quantum efficiency data to equivalent number density (equation (3)). Moreover, the algorithm further relates the equivalent number density to the quantum efficiency by a different integral operator so that an analytic, rather than a numerical, reconstruction obtains.

E. FLOW DIAGRAMS

Figure 5:
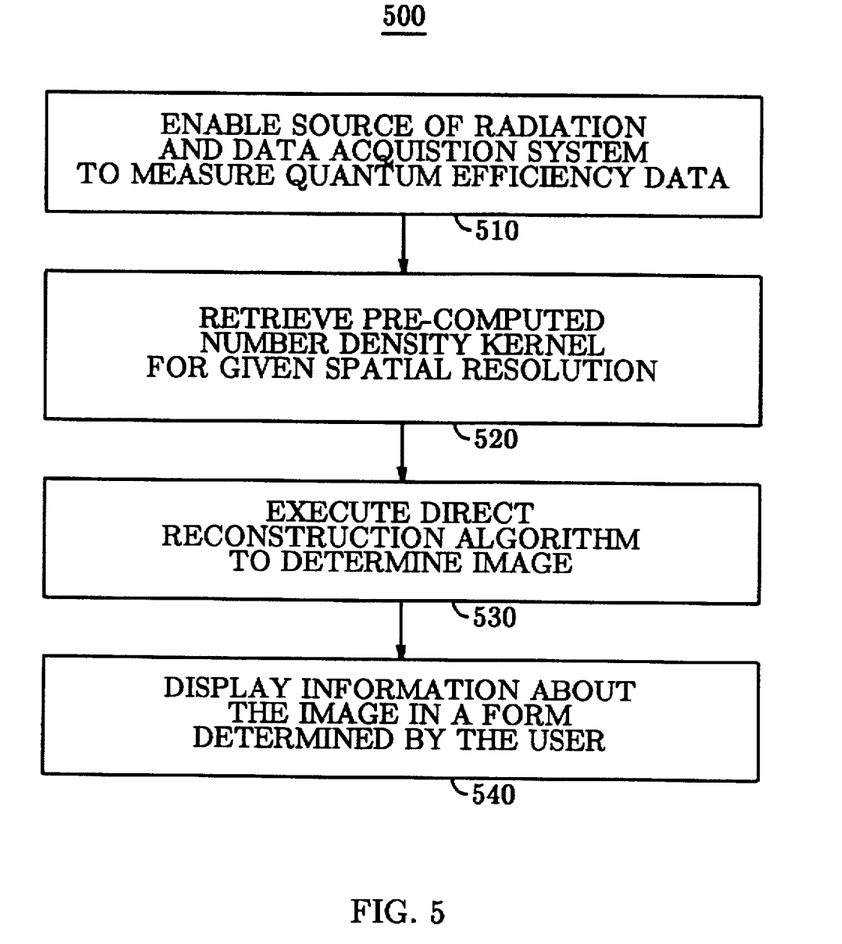
FIG. 5 is a flow diagram for the direct numerical solution for the number density.

The methodology discussed in the previous sub-section (A) is set forth in high-level flow diagram 500 in FIG. 5 in terms of the illustrative embodiment of the system shown in FIG. 4. With reference to FIG. 5, the processing effected by control block 510 enables photon source 420 and data acquisition system 430 so as to measure energy emanating from object 410 due to CW source 420 and reradiated from object 410 due to fluorescent emission. These measurements of quantum efficiency are passed to computer processor 450 from acquisition system 430 via bus 431. Next, processing block 520 is invoked to retrieve the pre-computed and stored number density kernel as expressed by equation (5). In turn, processing block 530 is operated to execute the direct reconstruction algorithm set forth with respect to equations (6)–(31), thereby determining the equivalent number density of object 410 given by $\alpha(\rho_1\rho_2)$. Finally, as depicted by processing block 540, the reconstructed image corresponding to the $\alpha(\rho_1,\rho_2)$ is provided to output device 470 in a form determined by the user; device 470 may be, for example, a display monitor or a more sophisticated three-dimensional video display device.

One illustrative manner of carrying out the direct reconstruction exhibited by block 420 is further depicted by high-level flow diagram 600 of FIG. 6. In particular, processing block 610 shows that the first step is to form the number density kernel matrix (the A matrix as determined by discretization, that is, $A_{ij}^m$ for m=1,2, . . . , M; i=1,2, . . . ,P; j=1,2, . . . ,Q, of equation (29)). Next, processing block 620 is invoked to compute the singular value decomposition of the kernel matrix A. Then, processing block 630 is executed to generate the regularized, generalized inverse $A^+$. Finally, block 640 is invoked to obtain the solution $a=A^+b$, where a represents the discretized values of the equivalent number density.

The system and methodology described to this point in the detailed description utilizes the free-space model of the number density kernel (equation (5)) so that the kernel is pre-computed and stored in computer processor 450 for recall during the reconstruction process. This is appropriate when object 410 is surrounded by an arrangement, such as a thin, rubber-like container filled with a a substance (e.g., the commercially available medical product called Intralipid), so that the arrangement provides a spatial extent external to the object that effectively gives rise to a free-space condition surrounding the object. The object's actual boundary (e.g., a human skull during imaging of brain) becomes merely another shape that is determined by the direct reconstruction procedure. Intralipid is useful because it is a colloidal substance wherein particles in the range of 0.5 microns to 2 microns are suspended, and the substance, as packaged, does not rapidly deteriorate; moreover, the l* of such a substance is readily measurable.

Figure 7:
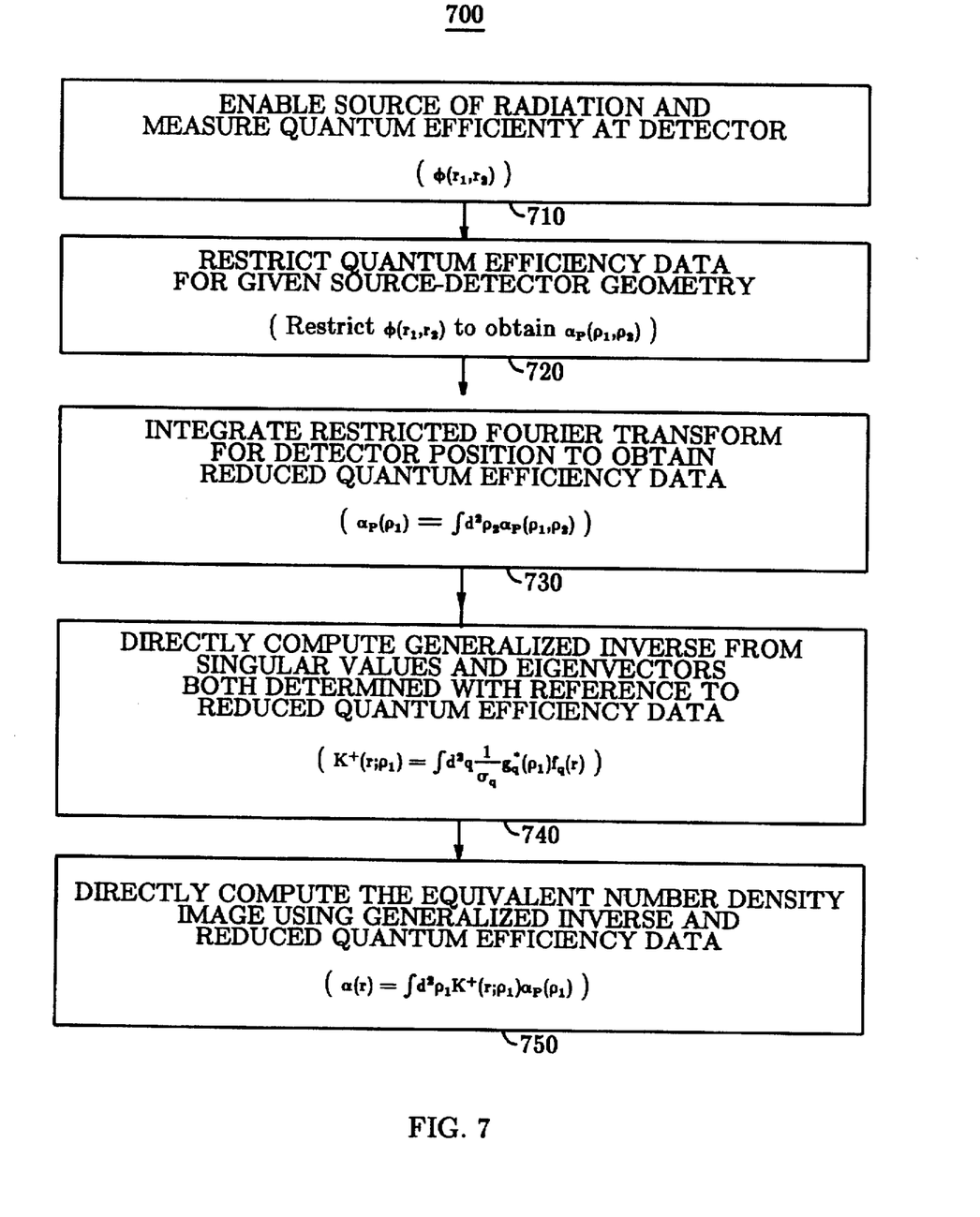
FIG. 7 is a flow diagram for the analytic, singular value decomposition solution for the equivalent number density.

The methodology discussed in the sub-section B is set forth in high-level flow diagram 700 in FIG. 7 in terms of the illustrative embodiment of the system shown in FIG. 4. With reference to FIG. 7, the processing effected by control block 710 enables source 420 and data acquisition system 430 so as to measure the quantum efficiency of object 410 resulting from the excitation diffusing wave and the reradiated diffusing wave. These measurements are passed to computer processor 450 from acquisition system 430 via bus 431. Next, as depicted by processing block 720, the quantum efficiency data is restricted to conform to the given source-detector geometry. Block 730 is invoked to integrate the Fourier transform of the restricted data over the detector position(s) to obtain the reduced quantum efficiency data. Following this integration, processing block 740 directly computes the generalized inverse from singular values and eigenvectors both determined with reference to the reduced quantum efficiency data. Lastly, processing block 750 is used to directly compute the equivalent number density $\alpha(r)$ using the generalized inverse and the reduced quantum efficiency data. The number density is presented on output device 470 in a form determined by the user; device 470 may be, for example, a display monitor or a more sophisticated three-dimensional video display device.

Whereas the above discussion has focused on reconstructing the number density for an object embedded in a homogeneous medium, that is, the absorption and diffusion coefficients/constants of the background and the object are the same, it is possible to reconstruct the number density representative of the object in an inhomogeneous medium as well. Now, instead of only one unknown (the number density), there are five unknowns, namely, the number density as well as the absorption and diffusion constants at the diffusing wave wavelength and at the reradiation diffusing wave wavelength. (It is also possible to introduce a sixth unknown—the fluorescent lifetime—since this lifetime may also provide useful information about the properties of the object under study). The fundamental integral equation (3) must be reformulated to account for the additional unknowns, and the solution methods become multi-dimensional rather than one-dimensional—which solution methods being straightforward as taught by the one-dimensional case.

It is to be understood that the above-described embodiment is simply illustrative of the application of the principles in accordance with the present invention. Other embodiments may be readily devised by those skilled in the art which may embody the principles in spirit and scope. Thus, it is to be further understood that the methodology described herein is not limited to the specific forms shown by way of illustration, but may assume other embodiments limited only by the scope of the appended claims.

What is claimed is:

1. A method for generating an image of an object comprising the steps of irradiating the object with a diffusing wave, measuring an intensity of a re-radiated diffusing wave to determine a quantum efficiency in terms of said diffusing wave and said re-radiated wave, wherein said quantum efficiency is related to the image by an integral operator, and directly reconstructing the image by executing a prescribed mathematical algorithm, determined with reference to said integral operator, on said quantum efficiency.

2. The method as recited in claim 1 wherein said algorithm further relates the image to said quantum efficiency by another integral operator.

3. A system for generating an image of an object comprising means for irradiating the object with a diffusing wave, means for measuring an intensity of a re-radiated diffusing wave to determine a quantum efficiency in terms of said diffusing wave and said re-radiated wave, wherein said quantum efficiency is related to the image by an integral operator, and means for directly reconstructing the image by executing a prescribed mathematical algorithm, determined with reference to said integral operator, on said quantum efficiency.

4. The system as recited in claim 3 wherein said algorithm further relates the image to said quantum efficiency by another integral operator, and wherein said means for directly reconstructing the image includes means for computing said algorithm with reference to both said integral operator and said another integral operator.

5. A method for generating an image of an object comprising the steps of irradiating the object with a diffusing wave, measuring a re-radiated diffusing waves relating both said diffusing wave and said re-radiated wave to the image by an integral operator, and directly reconstructing the image by executing a prescribed mathematical algorithm, determined with reference to said integral operator, on both said diffusing wave and said re-radiated wave.

6. The method as recited in claim 5 wherein said algorithm further relates the image to both said diffusing wave and said re-radiated wave by another integral operator.

* * * * *